United States Patent
Li et al.

(10) Patent No.: US 6,245,963 B1
(45) Date of Patent: Jun. 12, 2001

(54) KNOCKOUT-TRANSGENIC MOUSE MODEL OF SPINAL MUSCULAR ATROPHY

(75) Inventors: Hung Li; Hsiu-Mei Hsieh-Li; Jan-Gowth Chang, all of Taipei (TW)

(73) Assignee: Academia Sinica, Nankang, Taipei (TW)

(*) Notice: Subject to any disclaimer, the term of this patent is extended or adjusted under 35 U.S.C. 154(b) by 0 days.

(21) Appl. No.: 09/578,656

(22) Filed: May 25, 2000

Related U.S. Application Data

(60) Provisional application No. 60/136,520, filed on May 28, 1999.

(51) Int. Cl.$^7$ .................... A01K 67/00; A01K 67/027; G01N 33/00; C12N 15/00; C12N 15/87

(52) U.S. Cl. .................... 800/9; 800/18; 800/3; 800/22; 800/25; 435/455; 435/463; 435/320.1

(58) Field of Search .................... 800/3, 18, 22, 800/25, 8, 91; 435/455, 463, 320.1

(56) References Cited

PUBLICATIONS

Wong et al. The genetic and molecular mechanisms of motor neuron diseases, Curr. Opin. Neurobiol. 8:791–799, 1998.*
Gennarelli et al. Survival motor neuron gene transcript analysis in muscles from spinal muscular atrophy patients, Biochem. Biophys. Res. Commun. 213:342–348, 1995.*
Monani et al. The human centromeric survival motor neuron gene (SMN2) rescues embryonic lethality in Smn mice and results in a mouse with spinal muscular atrophy, Hum. Mol. Genet. 9:333–339, 2000.*
Fricker, J. Mouse model of spinal muscular atrophy, DDT 5:220–221, 2000.*
Lefebvre, S. et al. Identification and characterization of a spinal muscular atrophy–determining gene, *Cell* 80, 155–165 (1995).
Lefebvre et al., The role of the SMN gene in proximal spinal muscular atrophy, *Hum mol genet* 7, 1531–1536 (1998).
Hahene, et al., Hybrid Survival Motor Neuron Genes in Patients with Autosomal Recessive Spinal Muscular Atrophy: New Insights into Molecular Mechanisms Responsible for the Disease, *Am. J. Hum. Genet.* 59:1057–1065, (1996).
Steege et al. Apparent Gene Conversions Involving the SMN Gene in the Region of the Spinal Muscular Atrophy Locus on Chromosome 5, *Am. J. Hum. Genet.* 59:834–838, (1996).
Parsons, et al, Intragenic telSMN Mutations: Frequency, Distribution, Evidence of a Founder Effect, and Modification of the Spinal Muscular Atrophy Phenotype by cenSMN Copy No., *A M. J. Hum. Genet.* 63:1712–1723, (1998).
Lefebvre et al., Correlation between severity and SMN protein level in spinal muscular atrophy, *Nature genet* 16, 265–269 (1997).

Bergin et al., Identification and characterization of a mouse homologue of the Spinal Muscular Atrophy–determining gene, survival motor neuron, *Gene* 204:47–53 (1997).
Burghes, When is a Deletion Not a Deletion? When It Is Converted., *Am. J. Hum. Genet.* 61:9–15, (1997).
Melki, Spinal muscular atrophy, Current Opinion in Neurology 10:381–385, (1997).
Gavrilov et al. Differential SMN2 expression associated with SMA severity, *Nature genetics*, vol. 20, Nov. 1998.
Monani et al., A single nucleotide difference the alters splicing patterns distinguishes that SMA gene SMN1 from the copy gene SMN2, *Human Molecular Genetics*, vol. 8, No. 7 pp. 1177–1183 (1999).
Francis et al., Heterogeneity of subcellular localization and electriphoretic mobility of survival motor neuron (SMN) protein in mammalian neural cells and tissues, *Proc. Nat. Acad. Sci. USA.* vol. 95, pp. 6492–6497, May 1998.
La Bella et al., Survival motor neuron (SMN) protein in rat is expressed as different molecular forms and is developmentally regulated. *European Journal of Neuroscience*, vol. 10, pp. 2913–2923, (1998).
Burlet P. et al. The distribution of SMN protein complex in human fetal tissue and its alteration in spinal muscular atrophy, *Human Molecular Genetics*, vol. 7, No. 12 pp. 1927–1933 (1998).
Coovert et al., The survival motor neuron protein in spinal muscular atrophy, *Human Molecular Genetics*, vol. 6, No. 8 pp. 1205–1214 (1997).
Pellizzoni et al., SMN mutants of spinal muscular atrophy patients are defective in binding to snRNP proteins, *Proc. Natl. Acad. Sci. USA*, vol. 96, pp. 11167–11172 Sep. (1999).
Pellizzoni et al., A Novel Function for SMN, the Spinal Muscular Atrophy Disease Gene Product, in Pre–mRNA Splicing, *Cell*, vol. 95, pp. 615–624, Nov. 25, 1998.
Iwahashi et al., Synergistic anti–apoptotic activity between Bcl–2 and SMN implicated in spinal muscular atrophy, Nature vol. 390, pp. 413–417 Nov. 1997.

(List continued on next page.)

*Primary Examiner*—Karen M. Hauda
*Assistant Examiner*—Quang Nguyen
(74) *Attorney, Agent, or Firm*—Cohen, Pontani, Lieberman & Pavane

(57) ABSTRACT

A genetically engineered mouse model that genotypically and phenotypically mimics human patients with spinal muscular atrophy. The genome of the mouse model contains at least one mutation that knockouts the native mouse Smn gene and at least one copy of human SMN$^C$ gene that functions in a murine background and compensates for the loss of the functions provided by the Smn gene. The phenotypes of said mouse model can be grouped according to their severity of pathological conditions into three types, paralleling the three types of human spinal muscular atrophy conditions. Said mouse model can be used for studying the pathophysiology of spinal muscular atrophy and for developing and testing existing and new therapeutic and diagnostic methods.

15 Claims, 2 Drawing Sheets

OTHER PUBLICATIONS

Strasswimmer et al., Identification of survival motor neuron as a transcriptional activator–binding protein, *Human Molecular Genetics*, vol. 6, No. 8 pp. 1205–1214 (1997).

Campbell et al., Genomic Variation and Gene Conversion in Spinal Muscular Atrophy: Implications for Disease Process and Clinical Phenotype, *Am. J. Hum. Genet.* 61:40–50, (1997).

Chang et al., Molecular analysis of survival motor neuron (SMN) and neuronal apoptosis inhibitory protein (NAIP) genes of spinal muscular atrophy patients and their parents, Hum Gemet vol. 100: 577–581 (1997).

Li et al., Gsh–1 an orphan Hox gene, is required for normal pituitary development, The EMBO Journal, vol. 15, No. 4 pp. 714–724, (1996).

Hooper et al., HPRT–deficient (Lesch–Nyhan) Mouse Embryos derived from germline colonization by cultured cells, Nature vol. 326, pp 292–295 Mar. 19, 1987.

Hendrey et al., Developmental Analysis of the Hba$^{th-j}$ Mouse Mutation: Effects on Mouse Peri–Implantation Development and Identification of Two Candidate Genes, Developmental Biology, vol. 72, 253–263 (1995).

Zhang et al., Whole genome amplification from a single cell: Implications for genetic analysis, Proc. Natl. Acad. Sci. USA, vol. 89 pp 5847–58551, Jul. 1992.

Schreiber et al., Rapid detection of octamer binding proteins with 'mini–extracts', prepared from a small number of cells, *Nucleic Acids Research*, vol. 17, No. 15 pp 6419 (1989).

Laemmli, Cleavage of Structural Proteins during the Assembly of the Head of Bacteriophage T4, *Nature* vol., 227, pp 680–685, Aug. 15 (1970).

\* cited by examiner

# KNOCKOUT-TRANSGENIC MOUSE MODEL OF SPINAL MUSCULAR ATROPHY

RELATED APPLICATIONS

This application claims priority from U.S. Provisional Patent Application Serial No. 60/136,520 which was filed on May 28, 1999.

BACKGROUND OF THE INVENTION

1. Field of the Invention

The present invention relates to a mouse model for spinal muscular atrophy, or SMA, and to methods of making and using said mouse model. Particularly, the invention pertains to a genetically engineered mouse model which genotypically and phenotypically mimics human patients with spinal muscular atrophy. Said mouse model is useful in developing and evaluating various methods for diagnosing and treating human SMA patients.

2. Description of the Related Art

Spinal muscular atrophy (SMA) is an autosomal recessive disease characterized by degeneration of anterior horn cells of the spinal cord leading to muscular paralysis with muscular atrophy. Clinical diagnosis of the disease is based on progressive symmetric weakness and atrophy of the proximal muscles. Affected individuals are usually classified into three groups according to the age of onset and progression of the disease. Type I SMA, also known as Werdnig-Hoffnan disease, is most severe, and affected children usually show SMA symptoms before 6 months of age and rarely live beyond the age of 2 years. Type II and Type III SMA are less severe, and the onset of symptoms varies between 6 months and 17 years of age [see references 1–4]. SMA is one of the most common fetal autosomal recessive diseases, with a carrier rate of 1–3% in the general population and an incidence of 1 in 10,000 newborns [see references 5 and 8].

The pathological abnormality of SMA is the loss of motor neurons in the anterior horn of the spinal cord and in the brain stem, but the brain cortex is usually unaffected [see reference 9]. All three types of SMA are characterized by a marked decrease in deep reflexes and a diffused symmetric weakness of proximal muscles. Electromyographic analyses show muscle denervation with neither sign of sensory denervation nor major change in the motor nerve conduction velocity. Muscle denervation with atrophic fibers has been confirmed by muscle biopsy. Fiber groupings show features of muscle immaturity, suggesting an arrest in development [see references 10 and 11].

Irrespective of clinical severity, molecular analysis has shown that both types of the disease, whether it has a severe early onset or a mild late onset, are linked to the same chromosome locus 5q13, suggesting genetic homogeneity [see references 12–15]. Positional cloning strategies have led to the identification of two candidate genes for SMA, namely, survival motor neuron (SMN) and neuronal apoptosis inhibitory protein (NAIP) [see references 16 and 17]. These two genes are positioned within a complex region that is duplicated on the long arm of chromosome 5, resulting in two copies of NAIP (i.e., $NAIP^T$ and $NAIP^C$) and two copies of SMN (i.e., $SMN^T$ and $SMN^C$) in the human genome [see reference 18]. Deletion of NAIP exon 5 was found in 22–60% of type I SMA patients and in 5–18% of type II and III patients [see references 19–22]. Such deletion is also found in 3% of normal individuals, suggesting the gene is non-essential for motor neuron survival. In contrast, 95% of SMA patients carry homozygous deletions of $SMN^T$ regardless of phenotypic severity [see references 16, 19–21]. Telomeric SMN ($SMN^T$) and centromeric SMN ($SMN^C$) differ only in five nucleotides, none of which results in an amino acid change. Rarely, asymptomatic individuals show homozygous $SMN^T$ deletion [see references 19, 22–24]. SMNC deletion was found in 2–5% of normal populations [see references 16, 22]. Several intragenic mutations have been found in SMA patients with specific disruption in $SMN^T$, providing further evidence that $SMN^T$ is associated with SMA [see references 16, 18, 25–27]. The $SMN^C$ gene is also expressed in SMA patients, but expression pattern is different from that of $SMN^T$. Most $SMN^C$ transcripts lack exons 3, 5 or 7, particularly 7, while most $SMN^T$ transcripts appear to be full-length mRNAs [see references 28–29]. Dosage analysis shows that the SMN protein is significantly decreased in Type I patients [see references 30–31].

The SMN gene shows no homology to any previously identified genes. Recently, the SMN protein has been identified as one of the heterogeneous ribonucleoprotein U-associated proteins. The subsequent immunohistochemical analysis localized the SMN protein in a specific nuclear structure called gems [see references 32–33]. Based on the association of the gems and coiled bodies, a role of the SMN protein in RNA metabolism has been suggested and confirmed in an in vitro analysis [see reference 34]. Because the SMN gene is ubiquitously expressed in neuronal and non-neuronal tissues [see reference 16], the mechanism involved in specific degeneration of motor neurons, a characteristic feature of SMA, remains to be elucidated.

In addition to the lack of understanding of the pathophysiology of spinal muscular atrophy, there is no specific treatment currently available for SMA patients. Although transgenic mouse models have been utilized in studying various human diseases, including development of methods for diagnosis and treatment, no one has taught or suggested that a useful mouse model can be built for spinal muscular atrophy by knocking out the native mouse Smn gene and then rescuing the mouse with human $SMN^C$ gene inserted into the mouse genome.

The applicant hereby discloses an invention of a mouse model for spinal muscular atrophy. Said mouse model is genotypically and phenotypically mimic to human SMA patients and can be used to understand the pathophysiology of SMA and to develop methods of diagnosis and treatment of the disease. Part of the present invention was published in "A mouse model for spinal muscular atrophy", *Nature Genetics* 24, 66–70 (2000), the entire content of which is expressly incorporated herein.

CITED REFERENCES

1. Wohlfart, G., Fex, J., Eliasson, W. S. Hereditary proximal spinal muscular atrophy: a clinical entity simulating progressive muscular dystrophy. *Acta Psychiatr Neuro Scand* 30, 395–406 (1995).
2. Kugelberg, E, & Welander, L. Heredo-familial juvenile muscular atrophy simulating muscular dystrophy. *Arch Neuro Psych* 75, 500–509 (1956).
3. Dubowitz, V. Infantile muscular atrophy: a prospective study with particular reference to a slowly progressive variety. *Brain* 87, 707–718 (1964).
4. Pearn, J., Gardner-Medwin, D., Wilson, J. A. Clinical study of chronic childhood spinal muscular atrophy: a review of 141 cases. *J Neurol Sci* 37, 227–248 (1978).
5. Pearn J. The gene frequency of acute Werdnig-Hoffmann disease (SMA type I): a total population survey in northeast England. *J Med Genet* 10, 260–265 (1973).

6. Pearn, J. Incidence, prevalence, and frequency studies of chronic childhood spinal muscular atrophy. *J Med Genet* 15, 409–413 (1978).
7. Cziezel, A & Hamula J. Selective and non-selective susceptibility for muscle fiber types. *J. Med Genet* 26, 761–763 (1989).
8. Roberts D F, Chavez J, Court SDM. The genetic component in child mortality. *Arch Dis Child* 45, 33–38 (1970).
9. Shishikarak, K., Hara, M., Sasaki Y & Misagik, A neuropathologic study of Werding-Hoffinann disease with special reference to the thalamus and posterior roots. *Acta Neuropathol* 60, 99–106 (1983).
10. Engel, W. K. Selective and non-selective susceptibility for muscle fiber types. *Arch Neurol* 22, 97–117 (1970).
11. Fidzianska, A. Ultrastructural changes in muscle in spinal muscular atrophy-Werdnig-Hoffmann's disease. *Acta Neuropathol* 27, 247–256 (1974).
12. Brzustowicz, L. M. et al. Genetic mapping of chronic childhood-onset spinal muscular atrophy to chromosome 5q 11.2–11.3 *Nature* 344, 540–541 (1990).
13. Gilliam, T. C. et al. Genetic homogeneity between acute and chronic forms of spinal muscular atrophy. *Nature* 345, 823–825 (1990).
14. Melki, J. et al. Gene for chronic proximal spinal muscular atrophies maps to chromosome 5q. *Nature* 344, 767–768 (1990a).
15. Melki, J. et al. Mapping of acute (type I) spinal muscular atrophy to chromosome 5q12–q14. *Lancet* 336, 271–273 (1990b).
16. Lefebvre, S. et al. Identification and characterization of a spinal muscular atrophy-determining gene. *Cell* 80, 155–165 (1995).
17. Roy, N. et al. The gene for neuronal apoptosis inhibitory protein is partially deleted in individuals with spinal muscular atrophy. *Cell* 80, 167–178 (1995).
18. Lefebvre, S., Bŕglen, L., Frézal, J., Munnich, A. & Melki, J. The role of the SMN gene in proximal spinal muscular atrophy. *Hum Mol Genet* 7, 1531–1561 (1998).
19. Velasco E., Velero, C., Valero, A., Moreno, F. & Hernandez, C. C. Molecular analysis of the SMN and MAIP genes in Spanish spinal muscular atrophy (SMA) families and correlation between number of copies of CBCD 541 and SMA phenotype. *Hum Mol Genet* 5, 2570263 (1996).
20. Rodriguess, N. R. et aL Gene deletions in spinal muscular atrophy. *J Med Genet* 33, 93–96 (1996).
21. Burglen L. et al. The gene encoding P44, a subunit of the transcription factor TFIIH, is involved in large-scale deletions associated with Werdnig-Hoffman disease. *Am J Hum Genet* 60, 72–79 (1997).
22. Chang, J. G. et al. Molecular analysis of survival motor neuron (SMN) and neuronal apotosis inhibitory protein (NAIP) genes of spinal muscular atrophy patients and their parents. *Hum Genet* 100, 577–581 (1997).
23. Hahnen, E. et al. Molecular analysis of candidate genes on chromosome 5q 13 in autosomal recessive spinal muscular atrophy: evidence of homozygous deletions of SMN gene in unaffected individuals. *Hum Mol Genet* 4, 1927–1933 (1995).
24. Cobben, J. M. et al. Deletions of the survival motor neuron gene in unaffected siblings of patients with spinal muscular atrophy. *Am J Hum Genet* 57, 805–808 (1995).
25. Campbell, L., Potter, A., Ignatius, J., Dubowitz, V. & Davies, K. Genomic variation and gene conversion in spinal muscular atrophy: Implications for disease process and clinical phenotype. *Am J Hum Gemet* 61, 40–50 (1997).
26. Bussaglia, E. et al. A frame-slift deletion in the surival motor mevron gene in Spoanish spinal muscular atrophy patients. *Nutrue Genet* 11, 335–337 (1995).
27. Parsons, D. W., McAnchew, P. E. Innaccone, S. T., Mendel, J. R., Burghes, A. H. M. & Prior, T. W. Intragenic telSMN mutations; frequency, distribution, evidence of a founder effect, and modification of the spinal muscular atroph phenotype by cenSMN copy number. *Am J Hum Genet* 63, 1712–1723 (1998).
28. Gennarelli, M. et al. Survival motor newron gene transcripe analysis in muscles from spinal muscular atrophy patients. *Bioch Biophys Res Comm* 213, 342–348 (1995).
29. Chang, J. G. et al. Analysis of the MRNA products of the survival motor neuron (SMN) gene in peripheral blood mononuclear cells of normals. Cariers and SMA patients. *Am J Hum Gent* 59 (suppl), A252–1457 (1996).
30. Lefebvre, S. et al. Correlation between severity and SMN protein level in spinal muscular atrophy. *Nature genet* 16, 265–269 (1997).
31. Burlet P. et al. The distribution of SMN protein complex in human fetal tissues and its alteration in spinal muscular atrophy. *Hum Mol Genet* 7, 1927–1933 (1998).
32. Liu, Q., Fischer, V., Wang, F. & Dreyfuss, G. The spinal muscular atrophy disease gene product. SMN and its associated protein SIP1 are in a complex with spliceosonal snRNP protein. *Cell* 90, 1013–1021 (1997).
33. Fisher, V., Liu, Q. & Dreyfuss, G. The SMN-SIP1 complex has an essential role in the spliceosomal snRNP biogenesis. *Cell* 90, 1023–1029 (1997).
34. Pellizzoni, L., Kataoka, N., Charroux, B. & Dreyfuss, G. A novel function for SMN, the spinal muscular atrophy disease gene product, in pre-mRNA splicing. *Cell* 95, 615–624 (1998).

SUMMARY OF THE INVENTION

The present invention discloses a transgenic mouse model for spinal muscular atrophy. The genome of said mouse model carries at least one copy of human $SMN^C$ gene and a mutation that knockouts the native mouse Smn gene. Human $SMN^C$ gene is functional in a murine background and compensates for the loss of the Snm protein as evidenced by the rescue of the early lethality phenotype caused by the Smn knockout. The phenotypes of said mouse model are similar to those of SMA patients and can be subgrouped into three types according to their phenotypic severity. All these 3 types may be identified from at least two transgenic founder lines crossed with Smn knockout mice, indicating that these phenotypes are not caused by the position effect of the transgene. According to the present invention, the mouse model can be used for studying the pathophysiology of the disease. For example, using this mouse model, applicants have discovered that the severity of SMA-associated symptoms is proportionally related to the decrease in SMN protein production. This discovery is consistent with the prior hypothesis that the intact SMN protein is most important for phenotypic expression of the disease.

It is also an aspect of the present invention to use the transgenic mouse model for testing efficacy of various present and future therapeutic methods for spinal muscular atrophy, including drug and gene therapies as well as other therapeutic technologies. Drug therapy refers to the use of one or more chemical compounds to correct or alleviate pathological conditions at, in most cases, the cellular level, while genetic therapy generally refers to the method of correcting the underlying genetic defect at the DNA level, that is, by replacing the incorrect DNA sequences with the correct ones. Transgenic mice have been used for testing therapeutic efficacy for a wide variety of diseases and the general protocol is well known. Basically, the testing includes two steps. The first step is applying a therapy or a combination of therapies to a mouse model for a particular disease. The second step is to determine whether the pathological conditions characteristic of said disease is alleviated due to the application of the therapy. The therapeutic efficacy of a therapy can then be determined by comparing the pathological conditions shown in the same mouse model before and after applying the therapy, or by comparing the pathological conditions shown in the treated mice and untreated control mice.

Another aspect of the present invention is the use of the mouse model for testing the accuracy and sensitivity of diagnostic methods for spinal muscular atrophy. Specifically, said mouse model provides a convenient positive control necessary for developing and testing any diagnostic methods for spinal muscular atrophy.

It is further understood that, upon obtaining the mouse model of the present invention, people with ordinary skill in the art will be able to use the model for various practical purposes by making necessary variations and implementing certain details specific to the SMA mouse model.

In summary, one of the objectives of the present invention is to provide a mouse model for human spinal muscular atrophy. Another objective is to provide a method of understanding the pathophysiology of spinal muscular atrophy. A further objective is to provide a method of screening and testing new therapies for spinal muscular atrophy treatment and a method of designing and evaluating better means of diagnosis of spinal muscular atrophy.

Other objects and features of the present invention will become apparent from the following detailed description considered in conjunction with the accompanying drawings. It is to be understood, however, that the description and drawings are provided solely for purposes of illustration and not as a definition of the limits of the invention, for which reference should be made to the claims.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

In the drawings, like reference characters denote similar elements throughout the several views.

DETAILED DESCRIPTION OF THE PRESENTLY PREFERRED EMBODIMENTS

Figure 1:
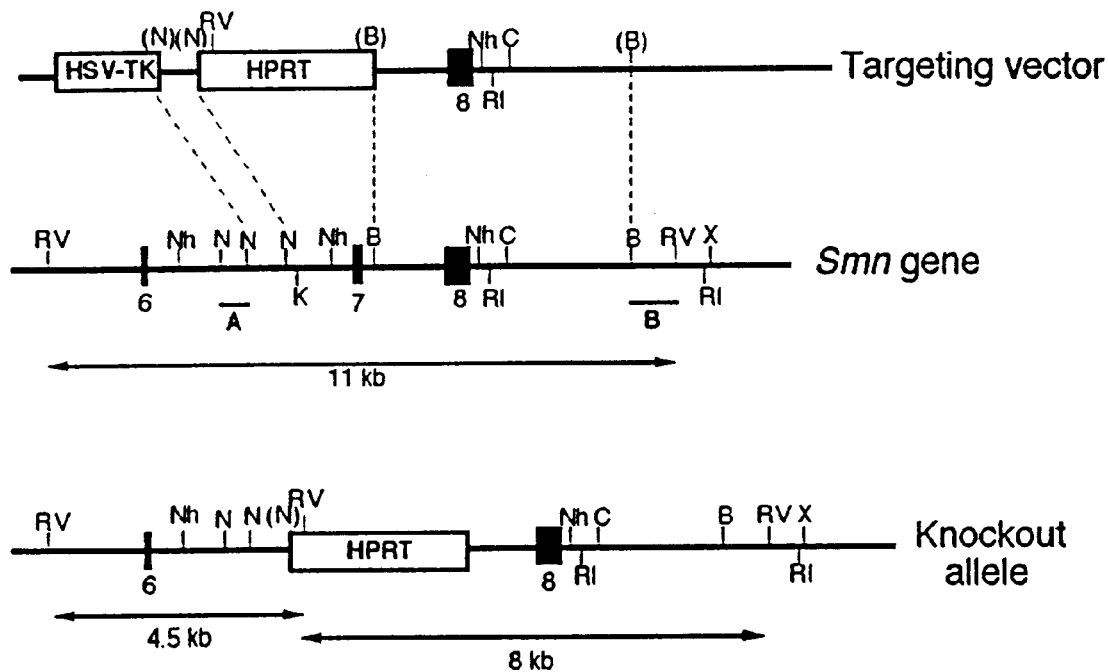
FIG. 1 is a diagram depicting the disruption of the mouse Smn gene with a targeting vector and the resulting knockout allele.
Figure 2:
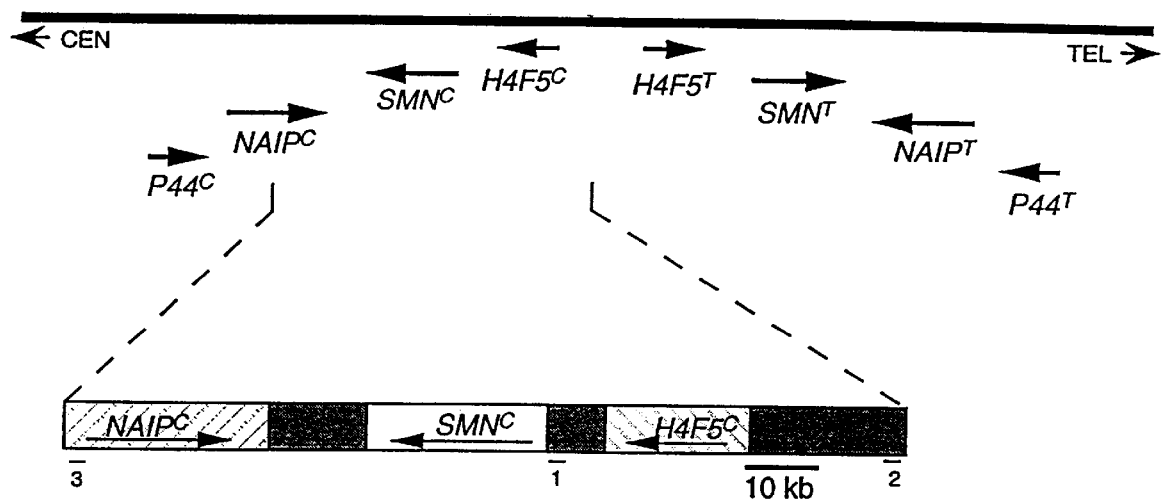
FIG. 2 is a diagram depicting the gene organization in the human SMN locus.

Isolation of Mouse Smn Genomic and Human SMN BAC Clones

The human SMN cDNA fragments A (covering exons 1–4) and C (covering exons 6–8) were used as probes to screen the mouse 129/Sv genomic (commercially available from Strategene) and human BAC libraries (available from Genome System). Three positive Smn genomic clones were isolated and subcloned into the pBS vector (available from Strategene). Four (4) positive BAC clones were classified as $SMN^C$ or $SMN^T$ by PCR-RFLP analysis as described by Cobben, J. M. et al. "Deletions of the survival motor neuron gene in unaffected siblings of patients with spinal muscular atrophy." Am J Hum Genet 57, 805–808 (1995).

Generation of Smn Knockout and $SMN^C$ Transgenic Mouse

To generate the Smn homologous recombination construction, a 4.6 kb BamHI fragment and a 0.6 kb NdeI fragment (covering Smn cDNA exons 2–8) of the mouse genomic clone MSG24-2, were subcloned into the BamHI and ClaI sites of pGKKOV vector, see Schrank, B. et al. "Inactivation of the survival motor neuron gene, a candidate gene for human spinal muscular atrophy, leads to massive cell death in early mouse embryos." Proc. Natl. Acad. Sci. USA 94, 9920–9925 (1997). The resulting construct, pGKKO-Smn, underwent a deletion of a 1.6 kb segment which includes the Smn exon 7. The final pGKKO-Smn construct was linearlized with NotI and then electroporated into E14 TG2a ES cells, see Hopper, M., Handy, K., Handyside A., Hunter, S., & Monk, M. "HPRT-deficient (Lesch-Nyhan) mouse embryos derived from qermline colonization by culture cells." Nature 326, 292–295 (1987). Selection and screening of ES cells for homologous recombination were performed as previously described by Schrank, B. et al. "Inactivation of the survival motor neuron gene, a candidate gene for human spinal muscular atrophy, leads to massive cell death in early mouse embryos." Proc. Natl. Acad Sci. USA 94, 9920–9925 (1997). The positive ES cells were then injected into C57BL/6 blastocysts by a standard procedure as described by Hogan, B., Beddington, R., Costantini, F. & Lacy, E. "Manipulating the mouse embryo. A laboratory manual." (1994), Cold Spring Harbor laboratory, Cold Spring Harbor, N.Y.

To generate $SMN^C$ transgenic mice, the vector sequence of SMN BAC clone 7C was excised with NotI and a resulting 115 kb DNA fragment (insert DNA), which encompasses O the human centromeric SMN ($SMN^C$) region including part of $NAIP^C$ and intact H4F5, was electroeluted from agarose gel. The insert DNA was diluted to 2 ng/l in 10 mM Tris-HCl pH7.4, 01 mM EDTA, and microinjected into PVB/N mouse male pronuclei as described by Hogan, B., Beddington, R., Costantini, F. & Lacy, E. Manipulating the mouse embryo. A laboratory manual (1994), Cold Spring Harbor laboratory, Cold Spring Harbor, N.Y.

Following the microinjection, five independent transgenic mice founder lines (FO) were generated in this particular case. The F0 mice appeared normal and the transgene was transmitted to F1 progenies. The F1 mice, who have the human transgene $SMN^C$ and are heterozygous for the mouse Smn locus ($Smn^{+/-}SMN^C$), were obtained from crossing the F0 founders to $Smn^{+/-}$ mice. Then, transgenic mice homozygous for the knockout alleles, i.e., $Smn^{-/-}SMNC$, were generated by F1 crossing with $Smn^{+/-}$ mice or F1 intercrossing.

Genotyping of Smn Knockout and $SMN^C$ Transgenic Mice

Smn knockout mice were genotyped by Southern blot or PCR analysis. Probes A and B, as shown in FIG. 1, were used in Southern blot analysis of mouse genomic DNA digested with NheI or EcoRV. Three primers were prepared for the PCR analysis: S1 (5'-ATAACACCACCACTCTTACTC-3')(SEQ ID NO.1), S2 (5'-GTAGCCGTGATGCCATTGTCA-3'; 1,150 bp)(SEQ ID NO.2), H1 (5'-AGCCTGAAGAACGAGATCAGC-3'; 950 bp)(SEQ ID NO.3). S1 and S2 were used for detection of the wild type alleles while S1 and H1 were used for detection of the knockout alleles. Further, another three sets of PCR primers were prepared for identifying transgenic mice: (1) 5'-ACTGCAACCTCCTGGGTTCAAGTG-3' (SEQ ID NO.4) and 5'-CAGTTCGAGACCAGCCTGACCAAT-3',(SEQ ID NO.5), probing the 5' untranslated region of SMN; (2) 5'-CGAATCACTTGAGGGCAGGAGTTTG-3'(SEQ ID NO.6) and 5'-AACTGGTGGACATGGCTGTTCATTG-3' (SEQ ID No.7), probing the 3' end of BAC clone; and (3) 5'-AAACCAGTCGGGCACAATACCTAGC-3'(SEQ ID NO.8) and 5'-TATGCTGATTGAAGGGAGGGGTGC-3' (SEQ ID NO.9, probing the 5' end of the BAC clone. The number of transgene copies in the transgenic mouse genome was determined in a Southern blot analysis by the amount of the probe (spanning SMN cDNA exons 3 and 4) that was hybridized to PstI-digested mouse genomic DNA.

Phenotypic Characterization of the $Smn^{-/-}SMN^C$ Mice

While the heterozygous $Smn^{+/-}SMN^C$ mice showed no gross morphological difference in comparison with normal mice, the $Smn^{-/-}SMN^C$ mice showed a wide range of symptoms, from early death to mild abnormalities. Grossly, these mice had lower body weights and shorter tails in comparison with their normal and heterozygote siblings, and could be classified into three groups according to their life span. Type I mice, the most severe type, died around day 10 without firry hair development; type II mice showed poor activity and died in 3–4 weeks; and type III mice survived and bred normally but had shorter and enlarged tails. About 50% of the type III mice developed chromic necrosis starting from the tip towards the root of the tail until the tail fell off. Such chronic necrosis was also be triggered when part of the tail is cut off for genotype analysis. The $Smn^{-/-}SMN^C$ mice of different types appeared in the same litter of identical parents.

Blastocyst Culture

Blastocysts from $Smn^{+/-}$mating were flushed out from the uterus on day 3.5 post coitum and cultured in Dulbecco's modified Eagle's medium (from Gibco, BRL) supplemented with 15% fetal bovine serum, 0.05 mM-mercaptoethanol and 1 mM glutamine at 37° C. in 5% $CO_2$. Individual blastocysts were cultured in separate plates coated with 0.15% gelatin in either the presence or the absence of $10^3$ units of LIF, see Hendrey, J., Lin D., and Dziadek, M. "Developmental Analysis of the Hba Mouse Mutation: Effects on mouse peri-implantation development and identification of two candidate genes." *Develop Biol.* 172, 253–263 (1995). Embryo morphology was monitored 3 or 4 times daily, and non-attached embryos were harvested into 5 μl of alkaline lysis buffer (200 mM KOH, 50 mM dithiothreitol) immediately after observing abnormal morphology. After 20 min incubation at 65° C., 5 μl neutralization solution (900 mM Tris-HCl, pH 8.3, 300 mM KCl, 200 mM HCl) was added to the harvested samples. 5 μl aliquots of the lysed and neutralized sample was taken for genotyping by PCR analysis as described by Zhang, L. et al. "Whole genome amplification from a single cell: Implications for genetic analysis." *Proc. Natl. Acad. Sci. USA* 89, 5847–5851 (1992). On the other hand, the attached and expanded embryos were scraped off the bottom of the plates after a 4-day culture and, in a similar fashion, lysed and prepared for PCR analysis.

Analysis of $SMN^C$ Transgene Expression in Mice.

Reverse transcription from total RNA was carried out using a random primer 5'-$TN_{10}$-3' and MMLV reverse transcriptase (from Promega). The resulting single-stranded cDNA was then PCR-amplified using one or three pairs of primers that covers the entire SMN coding region. The first primer pair, amplifying the fragment from the 5' untranslated region to exon 4, was a forward primer 5'-CGCTGCGCATCCGCGGGTTTGCTATGGC-3'(SEQ ID NO.10)(also referred as P1) and a reverse primer 5'-TCCCAGTCTTGGC-CCTGGCAT-3'(SEQ ID NO.11). The second primer pair, amplifying exons 4–6, was a forward primer 5'-AACATCAAGCCCAAATCTGC-3'(SEQ ID NO. 12) and a reverse primer 5'-GCCAGTATGATAGCCACTCATGTACCATG-3'(SEQ ID NO.13). The third primer pair, amplifying, exons 6–8 was a forward primer 5'-CTCCCATATGTCCAGATTCTCTTGATGATGC-3' (SEQ ID NO.14) and a reverse primer 5'-ACTGCCTCACCACCGTGCTGG-3'(SEQ ID NO. 15) (also referred as P6). In addition, P1 and P6 were used to amplify the full-length SMN cDNA.

The human $SMN^C$ transgene in the $Smn^{-/-}SMN^C$ mice were found expressed extensively in all the tissues analyzed. Like SMA patients, alternative splicing involving exons 3, 5 and 7 of the human $SMN^C$ gene was also observed in these mice. A majority of the transcripts also lacked exon 7. Transcripts without exon 3 or exon 5, and the full-length transcripts, were detected to a lesser extent. Among the three types of $Smn^{-/-}SMN^C$ mice, the ratio of full length transcripts versus alternatively spliced transcripts varied slightly. The early onset mice always produced fewer full-length transcripts, while mice with mild symptoms generally produced more full-length transcripts.

Subcellular Fractionation

Fresh frozen spinal cord and skeletal muscle samples (500 mg) from different transgenic mice were fractionated as described by Schreiber, E., Matthias, P., Muller, M. M. & Schaffner, W. "Rapid detection of octamer binding proteins with 'mini-extracts' prepared from a small number of cells." *Nucleic Acids Res.* 17, 6419 (1989). The tissues were homogenized with a tight-fitting glass pestle in ice-cold buffer A (10 mM Hepes, pH 7.9, 10 mM KCl, 0.1 mM EDTA, 0.1 mM EGTA, 1 mM DTT, 0.5 mM PMSF, 2 g/ml leupeptin, 2 g/ml pepstatin) with 0.5% Nonidet P-40 and kept on ice for 15 minutes. The nuclei were pelleted by centrifugation at 800g for 3 minutes, and resuspended by trituration in 100 1 l of buffer B (20 mM Hepes, pH 7.9, 0.4 M NaCl, 1 mM EDTA, 1 mM EGTA, 1 mM DTT, 1 mM PMSF, 2 glml leupeptin, 2 g/ml pepstatin), kept on ice for 15 minutes and then re-centrifuged at 15,000 g for 10 minutes at 4° C. The supernatant (soluble nuclear extract) was removed and the insoluble nuclear pellet was sonicated in a sonication buffer (100 mM Tris-HCl, pH 7.4, 1% SDS, 5 mM EDTA, 1 mM DTT, 1 mM PMSF, 2 g/ml leupeptin, 2 g/ml pepstatin).

Western-blot Analysis

Anti-human SMN antibodies were raised in rabbits against synthetic peptides encoded by parts of human SMN exon 7 (aa 279–288) and exon 2 (aa 72–84). Specific 20 antibodies (H2 and H7) from rabbit crude sera were purified with an EAH-Sepharose 4B column (from Pharmacia) according to the manufacturer's instructions.

Protein samples were loaded on a 5% polyacrylamide stacking gel above a 12% separating gel, and electrophoresis was carried out with a discontinuous buffer according to Laemmli, U. K. "Cleavage of structural proteins during assembly of the head of bacteriophage T4." *Nature* 227, 680–685 (1970). After electrophoresis the proteins were transferred electrophoretically from the gel to a polyvinyl difluoride membrane (from Millipore). The membrane was then blocked in TBST (50 mM Tris-HCl, pH 7.5, 150 mM NaCl, 0.05% Tween 20) containing 4% BSA for 2 hours at room temperature. The membrane was further incubated with a 1:800 dilution of anti-SMN exon 2 (H2) or anti-SMN exon 7 (H7) antibody in TBST for 2 hours at room temperature. The membrane was washed for three 20-minutes periods in TBST and was again incubated with a 1:32,000 dilution of an anti-rabbit IgG alkaline phosphatase conjugate (Sigma) in TBST for 1 hour at room temperature. The blot image was developed by adding 1.5% of 5-bromo-4-chloro-3-indoyl phosphate and 3% of nitro blue tetrazolium in a developing buffer (100 mM NaCl, 5 mM MgCl 2, 100 mM Tris-HCl, pH 9.5).

The results of western blot analysis showed that the decrease in the SMN protein production correlated proportionally with the severity of SMA-like symptoms in the $Smn^{-/-}$ $SMN^C$ mice. For example, Type I mice produced the least amount of the SMN protein in comparison with type II or type III mice.

Early Embryonic Lethality Caused by the Mutation in Smn

To create an Smn loss-of-function mutation via homologous recombination in mouse ES cells, applicants in this case isolated genomic clones of the mouse Smn locus by hybridization screening of an isogenic 129/Sv mouse genomic library using human SMN cDNA fragments corresponding to most of the exons as probes. Three clones were obtained which contained this genomic region. One of the clones, MSG24-2, which covers cDNA exons 2 to 8, was used to generate a targeting construct. A 4.6 kb and a 0.6 kb genomic fragments, flanking exon 7, were subcloned into the positive/negative selection targeting vector, pGKKOV, see Li, H., Zeitler, P. S., Valerius, M. T., Small, K. & Potter, S. S. "Gsh-1, an orphan Hox gene, is required for normal pituitary development." *EMBO J.* 15, 714–724 (1996)), to replace Smn exon 7 with the hypoxanthine phosphoribosyl-transferase (HPRT) cassette, see FIG. 1. After the resulting targeting construct, pKOV-Smn, was linearlized and electroporated into ES cells, applicants screened a total of 810 HAT/Ganciclovir-resistant ES clones with Southern blot or PCR analysis and, as a result, identified one clone which was heterozygous for Smn, i.e., $Smn^{+/-}$. The $Smn^{+/-}$ ES cells were then injected into C57 BL/6 blastocysts to obtain germline transmission of the mutant alleles. Mice heterozygous for Smn appeared normal. However, no viable homozygous mutant progenies ($Smn^{-/-}$) were obtained from intercrosses. The ratio between heterozygous and wild type mice was approximately 2:1. To examine the timing of development arrest, different stages of embryos from $Smn^{+/-}$ crossing were examined and normal ratios of homozygous E 3.5 blastocysts were found. However, there was no homozygotes found after E 6.5. When E 3.5 blastocyst were plated in vitro, wild type or heterozygous embryos hatched and attached during the first 1–2 days of culture to form an extended monolayer of polyploid, a giant trophoblast where the round cluster of inner cell mass (ICM) was attached. In contrast, homozygous mutants showed no attachment but extensive cellular degeneration during the first 12–36 hours of culture. This suggests that Smn plays an important role during early mouse development.

Histopathological Analysis

Mice were scarified with $CO_2$. Spinal cords and anterior spinal roots were fixed in 4% glutaraldehyde in 0.1 M cacodylate buffer, pH 7.4 for 2 hour at room temperature. After fixation, the tissues were washed in three changes of cacodylate buffer (0.1 M) for at least 20 minutes and then postfixed in 1% osmium tetroxide in 0.1 M cacodylate buffer for 1.5 hours at room temperature. The tissues were dehydrated using graded ethanol (50%, 70%, 90% and four changes of 100%) for 10 minutes each change, and then one change with propylene oxide for 5 minutes, one change with propylene oxide:epikote (1:1) for 1 hour, and lastly one change in epikote overnight at 4° C. The tissues were embedded in fresh epikote in polypropylene capsules and hardened at 60° C. for 48–72 hours. The tissues other than spinal cord were placed in 10 volumes of 10% neutral buffered formalin and embedded in paraffm. Serial frozen sections of mouse muscle were stained using histochemical methods including haematoxylin and eosin (H&E), modified Gomori trichrome, NADH-TR, routine ATPase, and ATPase with preincubation at pH 4.6 and 4.3 as described by Dubowitz, V. "Muscle Disorders in Childhood," W. B. Saunders, London (1995). Immunohistochemical staining was carried out according to Lefebvre, S. et al. "Correlation between severity and the SMN protein level in spinal muscular atrophy." *Nature Genet.* 16, 265–269 (1997).

Histopathological analysis of liver, spleen, kidney, heart, lung and gastrointestinal tract from the $Smn^{-/-}SMN^C$ mice showed no pathological abnormality. Pathological analysis of the tail tissue, however, revealed a decrease in muscular fiber, atrophic muscular bundles and subcutaneous edema. The subcutaneous edema was more severe in type III than other types, and it was rare in type I. The short and enlarged tails of type II and III mice show normal number of skeletal segments via X-ray analysis. Occasionally, decreased muscular fiber and atrophic muscular bundles were found in trunk muscles. The spinal cord showed a significant loss of large motor neurons in the anterior horns with an appearance of "empty-cell beds" in most of the severe type, and the remainder of the motor neurons occasionally showed central chromatolysis. There was a marked glial outgrowth and a selective loss thick myelinated fibers, with active axonal degeneration in both anterior and posterior spinal roots. These neurological defects are similar to the pathological features of SMA patients.

We claim:

1. A transgenic mouse whose genome comprises a homozygous disruption of an Smn gene such that said Smn gene does not produce functional Smn protein, wherein the mouse's genome additionally comprises a DNA sequence encoding human SMN protein, wherein expression of said DNA sequence encoding human SMN protein makes said mouse viable, said mouse showing one or more neurological defects similar to the pathological features of an SMN patient.

2. The transgenic mouse of claim 1, wherein said homozygous disruption in said Smn gene is a knockout mutation and said DNA sequence contains a copy of human $SMN^C$ gene.

3. The transgenic mouse of claim 2, wherein said knockout mutation comprises an insertion in said mouse Smn gene of a hypoxanthine phosphoribosyl-transferase cassette.

4. The transgenic mouse of claim 3, wherein said hypoxanthine phosphoribosyl-transferase cassette is inserted in exon 7 of said mouse Smn gene.

5. The transgenic mouse of claim 2, wherein said knockout mutation comprises a replacement of exon 7 of said mouse Smn gene by a hypoxanthine phosphoribosyl-transferase cassette.

6. A method of generating a transgenic mouse having a symptom of spinal muscular atrophy, comprising the steps of:

(a) generating a first line of mouse that has a heterozygous disruption for a mouse Smn locus ($Smn^{+/-}$);

(b) generating a second line of mouse whose genome possesses a human genomic DNA sequence having a copy of human $SMN^C$ gene;

(c) crossing a mouse of said second line with a mouse of said first line to obtain a third line of mouse with a genotype of $Smn^{+/-}SMN^C$; and (d) crossing a mouse of said third line with a mouse of said first line or intercrossing among mice of said third line to obtain a transgenic mouse having a symptom of spinal muscular atrophy, bearing a genotype of $Smn^{+/-}SMN^C$.

7. The method of claim 6, wherein said disruption is a knockout mutation.

8. The method of claim 7, wherein said knockout mutation is introduced by inserting in said mouse Smn a hypoxanthine phosphoribosyl-transferase cassette or by replacing exon 7 of said mouse Smn with a hypoxanthine phosphoribosyl-transferase cassette.

9. The method of claim 8, wherein said human genomic DNA sequence further comprises a copy of centromeric SERF1 and a portion of centromeric NAIP.

10. A method of testing for therapeutic efficacy of an agent on one or more symptoms of spinal muscular atrophy, said method comprising:

(a) applying one or more agents to be tested to a transgenic mouse of claim 2; and (b) determining whether one or more symptoms of spinal muscular atrophy have changed as a result of application of said agent or agents.

11. The method of claim 10, wherein said agent corrects genetic defects by changing one or more genomic DNA sequences of said transgenic mouse.

12. The method of claim 10, wherein said agent is a chemical compound which alleviates one or more symptoms of spinal muscular atrophy.

13. The method of claim 10, wherein said transgenic mouse is made according to claim 5.

14. The method of claim 13, wherein said agent corrects genetic defects by changing one or more genomic DNA sequences of said transgenic mouse.

15. The method of claim 13, wherein said agent is a chemical compound which alleviates one or more symptoms of spinal muscular atrophy.

* * * * *

SEQUENCE LISTING

<160> NUMBER OF SEQ ID NOS: 15

<210> SEQ ID NO: 1
<211> LENGTH: 21
<212> TYPE: DNA
<213> ORGANISM: Artificial Sequence
<220> FEATURE:
<223> OTHER INFORMATION: Primer for PCR

<400> SEQUENCE: 1
ataacaccac cactcttact c                                          21

<210> SEQ ID NO: 2
<211> LENGTH: 21
<212> TYPE: DNA
<213> ORGANISM: Artificial Sequence
<220> FEATURE:
<223> OTHER INFORMATION: Primer for PCR

<400> SEQUENCE: 2
gtagccgtga tgccattgtc a                                          21

<210> SEQ ID NO: 3
<211> LENGTH: 21
<212> TYPE: DNA
<213> ORGANISM: Artificial Sequence
<220> FEATURE:
<223> OTHER INFORMATION: Primer for PCR

<400> SEQUENCE: 3
agcctgaaga acgagatcag c                                          21

<210> SEQ ID NO: 4
<211> LENGTH: 24
<212> TYPE: DNA
<213> ORGANISM: Artificial Sequence
<220> FEATURE:
<223> OTHER INFORMATION: Primer for PCR

<400> SEQUENCE: 4
actgcaacct cctgggttca agtg                                       24

<210> SEQ ID NO: 5
<211> LENGTH: 24
<212> TYPE: DNA
<213> ORGANISM: Artificial Sequence
<220> FEATURE:
<223> OTHER INFORMATION: Primer for PCR

<400> SEQUENCE: 5
cagttcgaga ccagcctgac caat                                       24

<210> SEQ ID NO: 6
<211> LENGTH: 25
<212> TYPE: DNA
<213> ORGANISM: Artificial Sequence
<220> FEATURE:
<223> OTHER INFORMATION: Primer for PCR

<400> SEQUENCE: 6
cgaatcactt gagggcagga gtttg                                      25

<210> SEQ ID NO: 7
<211> LENGTH: 25
<212> TYPE: DNA
<213> ORGANISM: Artificial Sequence
<220> FEATURE:
<223> OTHER INFORMATION: Primer for PCR

<400> SEQUENCE: 7
aactggtgga catggctgtt cattg                                      25

<210> SEQ ID NO: 8
<211> LENGTH: 25
<212> TYPE: DNA
<213> ORGANISM: Artificial Sequence

```
<220> FEATURE:
<223> OTHER INFORMATION: Primer for PCR

<400> SEQUENCE: 8
aaaccagtcg ggcacaatac ctagc                                                    25

<210> SEQ ID NO: 9
<211> LENGTH: 24
<212> TYPE: DNA
<213> ORGANISM: Artificial Sequence
<220> FEATURE:
<223> OTHER INFORMATION: Primer for PCR

<400> SEQUENCE: 9
tatgctgatt gaagggaggg gtgc                                                     24

<210> SEQ ID NO: 10
<211> LENGTH: 28
<212> TYPE: DNA
<213> ORGANISM: Artificial Sequence
<220> FEATURE:
<223> OTHER INFORMATION: Primer for PCR

<400> SEQUENCE: 10
cgctgcgcat ccgcgggttt gctatggc                                                 28

<210> SEQ ID NO: 11
<211> LENGTH: 21
<212> TYPE: DNA
<213> ORGANISM: Artificial Sequence
<220> FEATURE:
<223> OTHER INFORMATION: Primer for PCR

<400> SEQUENCE: 11
tcccagtctt ggccctggca t                                                        21

<210> SEQ ID NO: 12
<211> LENGTH: 20
<212> TYPE: DNA
<213> ORGANISM: Artificial Sequence
<220> FEATURE:
<223> OTHER INFORMATION: Primer for PCR

<400> SEQUENCE: 12
aacatcaagc ccaaatctgc                                                          20

<210> SEQ ID NO: 13
<211> LENGTH: 29
<212> TYPE: DNA
<213> ORGANISM: Artificial Sequence
<220> FEATURE:
<223> OTHER INFORMATION: Primer for PCR

<400> SEQUENCE: 13
gccagtatga tagccactca tgtaccatg                                                29

<210> SEQ ID NO: 14
<211> LENGTH: 31
<212> TYPE: DNA
<213> ORGANISM: Artificial Sequence
<220> FEATURE:
<223> OTHER INFORMATION: Primer for PCR

<400> SEQUENCE: 14
ctcccatatg tccagattct cttgatgatg c                                             31
```

```
<210> SEQ ID NO: 15
<211> LENGTH: 21
<212> TYPE: DNA
<213> ORGANISM: Artificial Sequence
<220> FEATURE:
<223> OTHER INFORMATION: Primer for PCR

<400> SEQUENCE: 15
actgcctcac caccgtgctg g                                          21
```